(12) United States Patent
Norman et al.

(10) Patent No.: US 11,730,872 B2
(45) Date of Patent: Aug. 22, 2023

(54) HEIGHT ADJUSTMENT FOOT FOR MEDICAL DEVICES, STRUCTURES AND SYSTEMS INCLUDING SAME

(71) Applicants: Baxter International Inc., Deerfield, IL (US); Baxter Healthcare SA, Glattpark (CH)

(72) Inventors: John S. Norman, Gurnee, IL (US); Edward S. Szpara, St. Charles, IL (US); Anders Wellings, Belleair Beach, FL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 629 days.

(21) Appl. No.: 16/415,555

(22) Filed: May 17, 2019

(65) Prior Publication Data
US 2019/0351124 A1 Nov. 21, 2019

Related U.S. Application Data

(60) Provisional application No. 62/673,249, filed on May 18, 2018.

(51) Int. Cl.
*A61M 1/28* (2006.01)
*A61M 1/16* (2006.01)

(52) U.S. Cl.
CPC ............ *A61M 1/288* (2014.02); *A61M 1/166* (2014.02); *A61M 1/287* (2013.01); *A61M 1/285* (2013.01); *A61M 2205/123* (2013.01)

(58) Field of Classification Search
CPC ........ A61M 1/28–288; A61M 5/16818; A61M 2205/10; A61M 2205/12; A61M 2205/123; A61M 2205/18–186; A61M 2205/21; A61M 2205/215; A61M 2209/08; A61M 2209/084; A61M 2209/086; A47B 9/00–20; A47B 2009/003–145;
(Continued)

(56) References Cited

U.S. PATENT DOCUMENTS 1,437,670 A * 12/1922 Mazoch ................... A47B 9/00
                                                            248/423
4,539,005 A *  9/1985 Greenblatt .......... A61M 5/1483
                                                         248/222.51
(Continued)

*Primary Examiner* — Kami A Bosworth
(74) *Attorney, Agent, or Firm* — K&L Gates LLP

(57) ABSTRACT

A medical fluid delivery system includes a source of purified water; a source of concentrate for mixing with water from the water source; a disposable set including a pumping portion, a water line in fluid communication with the source of purified water and the pumping portion, the water line including a filter for filtering the water, a concentrate line in fluid communication with the concentrate source and the pumping portion, and a heater/mixing container in fluid communication with the pumping portion; a medical fluid delivery machine including, a pump actuator operable with the pumping portion of the disposable set, and a heater/mixing pan configured to support the heater/mixing container; and at least one leveling foot positioned and arranged to enable the heater/mixing pan to be oriented in a desired position for mixing the concentrate and purified water. A leveling tray and leveling foot are provided additionally.

13 Claims, 7 Drawing Sheets

(58) Field of Classification Search
CPC .............. A47B 2031/006; A47B 13/00; A47B 2200/0042; A47B 2200/0043; A47B 2200/0044
See application file for complete search history.

(56) References Cited

U.S. PATENT DOCUMENTS

| | | | | |
|---|---|---|---|---|
| 2001/0035702 | A1* | 11/2001 | Murphy | A61B 50/10 312/285 |
| 2007/0078370 | A1* | 4/2007 | Shener | A61M 3/022 604/8 |
| 2007/0276328 | A1* | 11/2007 | Childers | A61M 1/28 604/131 |
| 2011/0040242 | A1* | 2/2011 | Fallon | A61B 50/10 280/47.35 |
| 2013/0106609 | A1* | 5/2013 | Singh | A61M 1/288 248/676 |
| 2017/0319768 | A1* | 11/2017 | Szpara | A61M 1/284 |

* cited by examiner

HEIGHT ADJUSTMENT FOOT FOR MEDICAL DEVICES, STRUCTURES AND SYSTEMS INCLUDING SAME

RELATED APPLICATIONS

This application claims the benefit of and priority to U.S. Provisional Patent Application No. 62/673,249 filed May 18, 2018, entitled "HEIGHT ADJUSTMENT FOOT FOR MEDICAL DEVICES, STRUCTURES AND SYSTEMS INCLUDING SAME," which is incorporated herein by reference in its entirety.

BACKGROUND

The present disclosure relates generally to medical fluid devices. More specifically, the present disclosure relates to medical fluid devices that mix fluid online for treatment or that receive fluid mixed online for treatment.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney function is critical to many people because the treatment is life saving.

One type of kidney failure therapy is hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD (HF, HDF) treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products than a patient receiving less frequent but perhaps longer treatments. A patient receiving more frequent treatments does not experience as much of a down cycle as does an in-center patient, who has built-up two or three day's worth of toxins prior to a treatment. In certain areas, the closest dialysis center may be many miles from the patient's home, causing door-to-door treatment time to consume a large portion of the day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal cavity via a catheter. The dialysis fluid contacts the peritoneal membrane of the peritoneal cavity. Waste, toxins and excess water pass from the patient's bloodstream, through the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal cavity. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal cavity, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal cavity. APD machines also allow for the dialysis fluid to dwell within the cavity and for the transfer of waste, toxins and excess water to take place. The source may include multiple sterile dialysis fluid solution bags.

APD machines pump used or spent dialysate from the peritoneal cavity, though the catheter, and to the drain. As with the manual process, several drain, fill and dwell cycles occur during dialysis. A "last fill" may occur at the end of the APD treatment. The fluid may remain in the peritoneal cavity of the patient until the start of the next treatment, or may be manually emptied at some point during the day.

In any of the above modalities using an automated machine, treatment fluid may be prepared online or at the point of use, e.g., before and/or during the treatment. Here, purified water is typically mixed with a concentrate to prepare the treatment fluid online. To mix properly, it is important to handle the fluids being mixed with care. For example, if the concentrate has a higher density than the purified water, care should be taken that the place where the fluids are mixed does not include unwanted low points in which the heavier fluid may pool and not mix properly. A need exists accordingly to provide a way to ensure that a mixing area for mixing medical fluid components is done at a desired pitch of lack of pitch.

SUMMARY

The examples described herein disclose automated systems and methods applicable, for example, to fluid delivery for: peritoneal dialysis ("PD"), plasmapherisis, hemodialysis ("HD"), hemofiltration ("HF") hemodiafiltration ("HDF"), continuous renal replacement therapy ("CRRT"), apheresis, autotransfusion, hemofiltration for sepsis, and extracorporeal membrane oxygenation ("ECMO") treatments. The systems and methods described herein are applicable to any medical fluid delivery system in which the treatment fluid may be made online or at the point of use, e.g., just before and/or during treatment. These modalities may be referred to collectively or generally individually herein as medical fluid delivery system(s).

Moreover, each of the systems and methods described herein may be used with clinical or home-based treatments. For example, the present systems and methods may be employed in in-center PD, HD, HF or HDF machines, which run throughout the day. Alternatively, the present systems and methods may be used with home PD, HD, HF or HDF machines, which are operated generally at the patient's convenience.

In one embodiment, a peritoneal dialysis system and method are provided having point of use dialysis fluid production. The system includes a cycler and a water purifier. The cycler includes a control unit having at least one processor and at least one memory. The cycler may further include a wired or wireless transceiver for sending information to and receiving information from the water purifier. The water purifier may also include a control unit having at least one processor and at least one memory and a wired or wireless transceiver for sending information to and receiving information from the control unit of the cycler.

The cycler includes equipment programmed via its control unit to prepare fresh dialysis solution at the point of use, pump the freshly prepared dialysis fluid to a patient, allow the dialysis fluid to dwell within the patient, then pump used dialysis fluid to a drain. The cycler in one embodiment includes a heater under control of the control unit for heating the dialysis fluid as it is being mixed. The heater may for example be placed in a heater/mixing pan at the top of a housing of the cycler, e.g., beneath a heating lid.

The cycler (and the water purifier in one embodiment) operates with a disposable set. The disposable set may include a disposable pumping cassette, which may be provided with a planar rigid plastic piece covered on one or both sides by a flexible membrane, forming fluid pumping and valving chambers. The fluid pumping chambers may operate with pneumatic pump chambers of the cycler, while fluid valve chambers operate with the pneumatic valve chambers of the cycler.

The disposable set may include (i) a patient line that extends from the cassette to a patient line connector, (ii) a drain line that extends from the cassette to a drain line connector (which may in turn connect removeably to the water purifier), (iii) a heater/mixing line that extends from the pumping cassette to a heater/mixing bag, (iv) an upstream water line segment that extends from the water purifier to a water inlet of a water accumulator and a downstream water line segment that extends from a water outlet of the water accumulator to the cassette, (v) a last bag or sample line that extends from the cassette to a premixed last fill bag of dialysis fluid or to a sample bag or other sample collecting container, (vi) a first, e.g., glucose, concentrate line extending from the cassette to a first, e.g., glucose, concentrate container, and/or (vii) a second, e.g., buffer, concentrate line that extends from the cassette to a second, e.g., buffer, concentrate container.

In an embodiment, the upstream water line segment includes one or more sterilizing grade filter that further filters water exiting the water purifier to ensure that the water is made suitable for a peritoneal dialysis treatment ("WFPD") in case the water purifier itself is not able to do so. Redundant sterilizing grade filters are provided in an embodiment in case one of the filters fails.

The heater/mixing pan may be angled so that the heater/mixing bag is likewise angled for optimal mixing, heating and/or for air collection. Alternatively, it may be desired that the heater/mixing pan be as flat as possible. In either case, it is likely that when the cycler or medical fluid delivery machine is placed on a table or other supporting structure, that the cycler or machine will not be at the desired pitch or level due to inconsistencies with the supporting structure and/or the ground beneath the supporting structure. It is accordingly contemplated to incorporate leveling feet with the medical fluid delivery system, either directly with a housing of the cycler or machine or with a leveling tray placed in between the cycle or machine and the supporting structure.

The leveling feet are in one embodiment telescoping leveling feet. The leveling feet may include an inner cylindrical member having internal female threads, external male threads, and a graspable circular flange that extends outwardly from a base the first external male threads. An outer cylindrical member is provided including its own internal female threads sized to receive the external male threads of the inner cylindrical member and its own external male threads for threading into mating female threads of a structure attaching the leveling foot. The structure may again be the machine or cycler or a leveling tray. The outer cylindrical member also includes its own graspable circular flange extending outwardly from a base of the external male threads of the outer member.

The leveling feet are configured such that the flange of the outer member is turned by a user to move the outer cylindrical member relative to the inner cylindrical member for first level adjustment and the flange of the inner member is turned by the user to move the structure relative to the inner and outer cylindrical members for second level adjustment. In an embodiment, it does not matter in which order the user performs the first or second level adjustment.

A tightening member is provided to tighten or lock the inner cylindrical member to the outer cylindrical member, and the outer cylindrical member to the structure attaching the leveling foot when the leveling foot is in a desired leveling position. The tightening member is in one embodiment a screw, such as a flathead screw, which may be adjusted from above a surface of the medical device or leveling tray. Either one or both of the inner cylindrical member or the outer cylindrical member may be provided with one or more slit and/or one or more weakened section, so that the members deform at desired locations when the tightening member is tightened (e.g., screw threaded into inner member) and relax when the tightening member is loosened (e.g., screw threaded out of inner member).

The leveling tray when used may also be provided with a number of additional features including hooks with which to hang objects, such as medical fluid bags or containers, e.g., purified water and concentrate containers associated with the point of use medical fluid production system of the present disclosure. The hooks may be formed integrally with a surface of the tray. The tray surface may alternatively be formed with hook receiving locations, e.g., hook receiving openings, onto or into which the hooks are selectively fitted. Here, the hooks are loose pieces that may be placed where desired. Another additional tray feature includes the provision of indents on the tray surface for receiving at least a portion of an object placed upon the receiving tray such that the object is urged against sliding along the tray surface. The object may be the medical fluid device or cycler of the present disclosure, which has mounting feet, wherein the indents are circular or similarly indents sized to receive the mounting feet and to tend to prevent the feet from sliding along the surface of the tray.

One or more level detector may be incorporated with the cycler or machine and/or with the leveling tray. Multiple level detectors may be provided to level the cycler or machine along multiple, e.g., length and depth, directions. The level detectors may be visually interrogated bubble detectors known to those of skill. The level detectors may alternatively be electrically outputting single or multiple dimension laser, bubble, load cell or other type of detectors, which may be provided with and output to the control unit of the cycler or machine, which may in turn communicate with a user interface of the cycler or machine. The user interface may provide an audio, visual or audiovisual message guiding the user as to which leveling foot to adjust and in which direction. When the electrically outputting level detector senses that the cycler or machine is in a desired leveling position, or within a specified percentage of same, the user interface so notifies the user.

In light of the disclosure herein and without limiting the disclosure in any way, in a first aspect of the present disclosure, which may be combined with any other aspect listed herein unless specified otherwise, a medical fluid delivery system includes a source of purified water; a source of concentrate for mixing with water from the water source; a disposable set including a pumping portion, a water line in fluid communication with the source of purified water and the pumping portion, a concentrate line in fluid communication with the concentrate source and the pumping portion, and a mixing container in fluid communication with the pumping portion; a medical fluid delivery machine including, a pump actuator operable with the pumping portion of the disposable set, and a mixing pan configured to support the heater/mixing container; and at least one leveling foot positioned and arranged to enable the mixing pan to be oriented in a desired position for mixing the concentrate and purified water.

In a second aspect of the present disclosure, which may be combined with any other aspect listed herein unless specified otherwise, the at least one leveling foot is connected to a housing of the medical fluid delivery machine.

In a third aspect of the present disclosure, which may be combined with any other aspect listed herein unless specified otherwise, the medical fluid delivery system includes a leveling tray upon which the medical fluid delivery machine is set for treatment, and wherein the at least one leveling foot is connected to the leveling tray.

In a fourth aspect of the present disclosure, which may be combined with the third aspect in combination with any other aspect listed herein unless specified otherwise, the leveling tray is provided with at least one hook for supporting at least one fluid container, such as a container for the concentrate source.

In a fifth aspect of the present disclosure, which may be combined with the fourth aspect in combination with any other aspect listed herein unless specified otherwise, the source of purified water includes a water purifier or a container for the purified water, the at least one hook configured to support the container for the purified water.

In a sixth aspect of the present disclosure, which may be combined with the fourth aspect in combination with any other aspect listed herein unless specified otherwise, the leveling tray includes at least one hook receiving location positioned and arranged to removeably receive the at least one hook.

In a seventh aspect of the present disclosure, which may be combined with the third aspect in combination with any other aspect listed herein unless specified otherwise, the leveling tray includes a border extending from the medical fluid delivery machine, the border forming at least one aperture allowing access to adjust the at least one leveling foot.

In an eighth aspect of the present disclosure, which may be combined with the third aspect in combination with any other aspect listed herein unless specified otherwise, the medical fluid delivery machine or the leveling tray includes a level detector.

In a ninth aspect of the present disclosure, which may be combined with any other aspect listed herein unless specified otherwise, the medical fluid delivery machine includes a control unit and a level detector in operable communication with the control unit.

In a tenth aspect of the present disclosure, which may be combined with the ninth aspect in combination with any other aspect listed herein unless specified otherwise, the medical fluid delivery machine includes a user interface in operable communication with the control unit, the control unit configured to generate at least one audio, visual or audiovisual message via the user interface based upon communication with the level detector.

In an eleventh aspect of the present disclosure, which may be combined with any other aspect listed herein unless specified otherwise, a leveling tray includes a surface defining at least one aperture; and a leveling foot provided beneath each aperture, the leveling foot including a first member, a second member moveable translationally relative to the first member to provide leveling adjustment, and a tightening member accessible by a user from above the aperture, the tightening member positioned and arranged for the user to tighten the first member against the second member when the user has moved the second member to a desired translational location relative to the first member.

In a twelfth aspect of the present disclosure, which may be combined with the eleventh aspect in combination with any other aspect listed herein unless specified otherwise, the surface further defines at least one object receiving indent configured to receive at least a portion of an object placed upon the leveling tray.

In a thirteenth aspect of the present disclosure, which may be combined with the eleventh aspect in combination with any other aspect listed herein unless specified otherwise, the leveling tray includes (i) at least one hook receiving location positioned and arranged to removeably receive at least one hook or (ii) an integrally formed at least one hook.

In a fourteenth aspect of the present disclosure, which may be combined with the eleventh aspect in combination with any other aspect listed herein unless specified otherwise, the surface is further configured to receive the leveling foot such that the surface is moveable translationally relative to the first and second members to provide additional leveling adjustment.

In a fifteenth aspect of the present disclosure, which may be combined with the fourteenth aspect in combination with any other aspect listed herein unless specified otherwise, the first member is cylindrical and defines first female threads sized to receive male threads of the tightening member and first male threads, and wherein the second member is cylindrical and defines second female threads sized to receive the first male threads of the first member and second male threads sized to be threaded into female threads provided by the surface of the tray.

In a sixteenth aspect of the present disclosure, which may be combined with any other aspect listed herein unless specified otherwise, a leveling foot includes an inner cylindrical member including first internal female threads and first external male threads and a first flange extending outwardly from the first external male threads; an outer cylindrical member including second internal female threads sized to receive the first external male threads of the inner cylindrical member and second external male threads for threading into mating female threads of a structure attaching the leveling foot, the outer cylindrical member further including a second flange extending outwardly from the second external male threads; the foot configured such that the second flange is turned by a user to move the outer cylindrical member relative to the inner cylindrical member for first level adjustment and the first flange is turned by the user to move the structure relative to the inner and outer cylindrical members for second level adjustment; and a tightening member including third male threads sized to be threaded into the first female threads provided by the inner cylindrical member.

In a seventeenth aspect of the present disclosure, which may be combined with the sixteenth aspect in combination with any other aspect listed herein unless specified otherwise, the tightening member includes a head configured to be grasped and turned by the user to tighten or loosen at least one of (i) the inner cylindrical member relative to the outer cylindrical member, or (ii) the outer cylindrical member relative to the structure attaching the leveling foot.

In an eighteenth aspect of the present disclosure, which may be combined with the sixteenth aspect in combination with any other aspect listed herein unless specified otherwise, the inner cylindrical member includes plural slits forming plural cylindrical sections that hinge outwardly when the tightening member is threaded into the first female threads provided by the inner cylindrical member.

In an nineteenth aspect of the present disclosure, which may be combined with the eighteenth aspect in combination with any other aspect listed herein unless specified otherwise, the outer cylindrical member includes a slit enabling the outer cylindrical member to spread open when the plural cylindrical sections of the inner cylindrical member hinge outwardly.

In a twentieth aspect of the present disclosure, which may be combined with the nineteenth aspect in combination with any other aspect listed herein unless specified otherwise, the outer cylindrical member further includes at least one weakening groove enabling the outer cylindrical member to spread open about the at least one weakening groove.

In a twenty-first aspect of the present disclosure, any of the structure, functionality and alternatives disclosed in connection with FIGS. 1 to 10 may be combined with any of the other structure, functionality and alternatives disclosed in connection with FIGS. 1 to 10.

In light of the present disclosure and the above aspects, it is therefore an advantage of the present disclosure to provide an improved medical fluid delivery system.

It is another advantage of the present disclosure to provide an improved medical fluid delivery system that prepares treatment fluid online or at the point of use.

It is a further advantage of the present disclosure to provide improved leveling feet, e.g., for a medical fluid delivery system, having efficient height adjustment via a telescoping arrangement.

It is yet another advantage of the present disclosure to provide improved leveling feet, e.g., for a medical fluid delivery system, which show less threads due to a telescoping thread arrangement.

It is yet a further advantage of the present disclosure to provide improved leveling feet, e.g., for a medical fluid delivery system, in which locking the feet in place is performed conveniently from above and does not require a locking nut, which would consume thread space that may otherwise be used for height adjustment.

It is still another advantage of the present disclosure to provide improved leveling feet, e.g., for a medical fluid delivery system, which at least in certain embodiments avoids side set-screw locking.

It is still a further advantage of the present disclosure to provide improved leveling feet that may be used in many different types of applications.

Moreover, it is an advantage of the present disclosure to provide a leveling tray having multiple useful features, such as selectably placeable bag hanging hooks and machine mounting indents.

The advantages discussed herein may be found in one, or some, and perhaps not all of the embodiments disclosed herein. Additional features and advantages are described herein, and will be apparent from, the following Detailed Description and the figures.

DETAILED DESCRIPTION

System Overview

The examples described herein are applicable to any medical fluid therapy system that delivers a medical fluid that may be mixed at the point of use, prior to and/or during treatment, such as dialysis fluid, substitution fluid, or an intravenous drug. The examples are particularly well suited for kidney failure therapies, such as all forms of peritoneal dialysis ("PD"), hemodialysis ("HD"), hemofiltration ("HF"), hemodiafiltration ("HDF") and continuous renal replacement therapies ("CRRT"), referred to herein collectively or generally individually as renal failure therapy. Moreover, the machines described herein may be used in clinical or home settings. For example, the machines and associated methods may be employed in an in-center PD or HD machine, which runs virtually continuously throughout the day. Alternatively, the machine and methods may be used in a home PD or HD machine, which can for example be run at night while the patient is sleeping. The machines and methods discussed herein are also applicable to medical delivery applications. The following examples will be described in the setting of a peritoneal dialysis system having point of use dialysis fluid production but may instead be used to make point of use treatment fluid for any of the above modalities.

Figure 1:
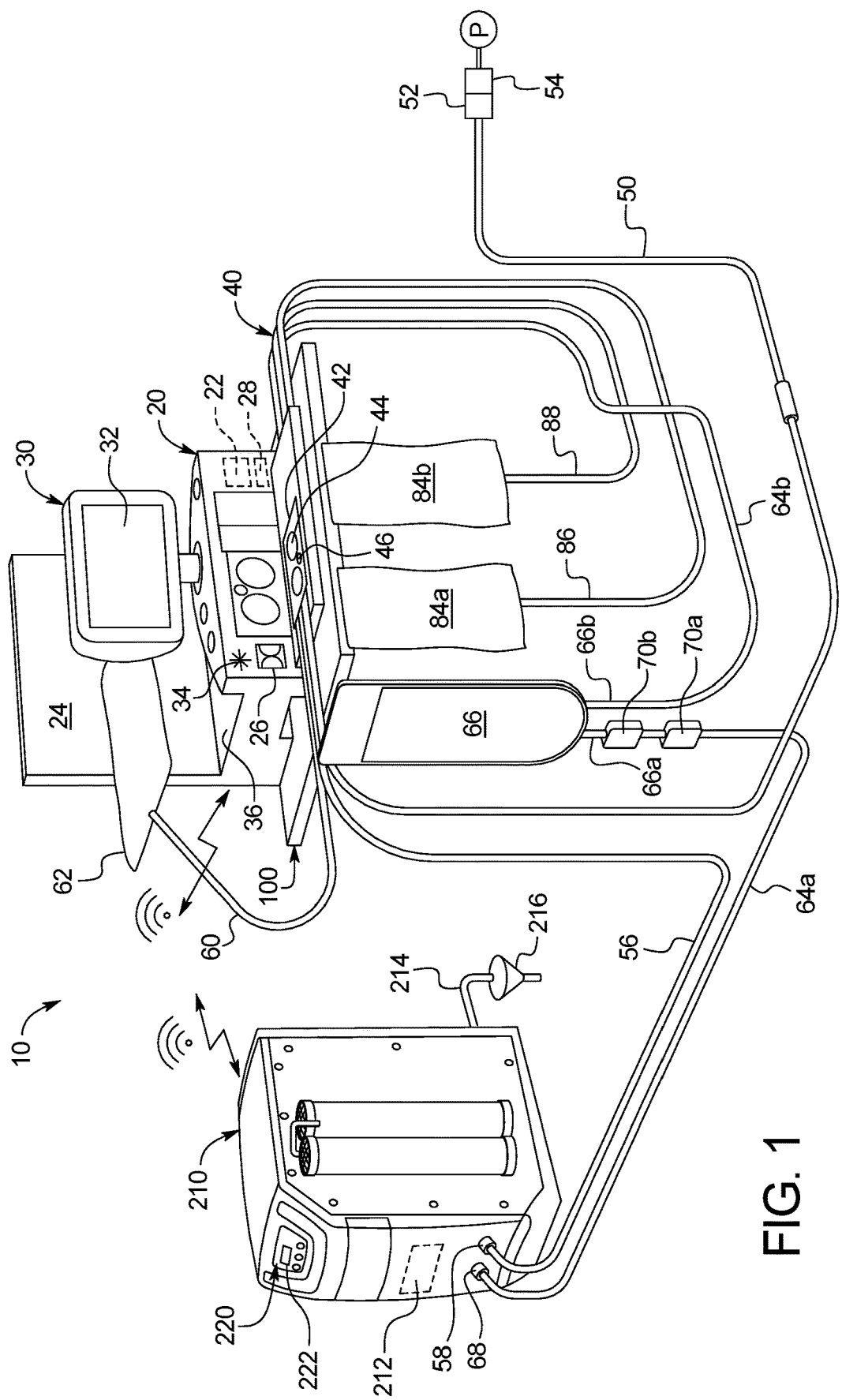
FIG. 1 is a top-front perspective view of one embodiment of a medical fluid delivery system having point of use dialysis fluid production and machine leveling of the present disclosure.

Referring now to the drawings and in particular to FIG. 1, one embodiment of a peritoneal dialysis system having point of use dialysis fluid production of the present disclosure is illustrated by system 10. System 10 includes a cycler 20 and a water purifier 210. Suitable cyclers for cycler 20 include, e.g., the Amia® or HomeChoice® cycler marketed by Baxter International Inc., with the understanding that those cyclers are provided with updated programming to perform and use the point of use dialysis fluid produced according to system 10. To this end, cycler 20 includes a control unit 22 having at least one processor and at least one memory. Control unit 22 further includes a wired or wireless transceiver for sending information to and receiving information from a water purifier 210. Water purifier 210 also includes a control unit 212 having at least one processor and at least one memory. Control unit 212 further includes a wired or wireless transceiver for sending information to and receiving information from control unit 22 of cycler 20. Wired communication may be via Ethernet connection, for example. Wireless communication may be performed via any of Bluetooth™, WiFi™, Zigbee®, Z-Wave®, wireless Universal Serial Bus ("USB"), or infrared protocols, or via any other suitable wireless communication technology.

Cycler 20 includes a housing 24, which holds equipment programmed via control unit 22 to prepare fresh dialysis solution at the point of use, pump the freshly prepared dialysis fluid to patient P, allow the dialysis fluid to dwell within patient P, then pump used dialysis fluid to a drain. In the illustrated embodiment, water purifier 210 includes a drain line 214 leading to a drain 216, which can be a house drain or a drain container. The equipment programmed via control unit 22 to prepare fresh dialysis solution at the point of use in an embodiment may include equipment for a pneumatic pumping system, including but not limited to (i) one or more positive pressure reservoir, (ii) one or more negative pressure reservoir, (iii) a compressor and a vacuum pump each under control of control unit 22, or a single pump creating both positive and negative pressure under control of control unit 22, to provide positive and negative pressure to be stored at the one or more positive and negative pressure reservoirs, (iv) plural pneumatic valve chambers for delivering positive and negative pressure to plural fluid valve chambers, (v) plural pneumatic pump chambers for delivering positive and negative pressure to plural fluid pump chambers, (vi) plural electrically actuated on/off pneumatic solenoid valves under control of control unit 22 located between the plural pneumatic valve chambers and the plural fluid valve chambers, (vii) plural electrically actuated variable orifice pneumatic valves under control of control unit 22 located between the plural pneumatic pump chambers and the plural fluid pump chambers, (viii) a heater under control of control unit 22 for heating the dialysis fluid as it is being mixed in one embodiment, and (ix) an occluder 26 under control of control unit 22 for closing the patient and drain lines in alarm and other situations.

As discussed in more detail below, housing 24 of machine or cycler 20 may further include an electrically outputting single or multiple dimension laser, bubble, load cell or other type of level detector 28, which may be provided with, and output to, control unit 22. In the illustrated embodiment, electrically outputting level detector 28 may be mounted on a printed circuit board ("PCB"), which is in electrical and/or data communication with one or more PCB of control unit 22.

In one embodiment, the plural pneumatic valve chambers and the plural pneumatic pump chambers are located on a front face or surface of housing 24 of cycler 20. The heater is located inside housing 24 and in an embodiment includes heating coils that contact a heating pan or tray, which is located at the top of housing 24, beneath a heating lid (not seen in FIG. 1).

Cycler 20 in the illustrated embodiment includes a user interface 30. Control unit 22 in an embodiment includes a video controller, which may have its own processing and memory for interacting with primary control processing and memory of control unit 22. User interface 30 includes a video monitor 32, which may operate with a touch screen overlay placed onto video monitor 32 for inputting commands via user interface 30 into control unit 22. User interface 30 may also include one or more electromechanical input device, such as a membrane switch or other button. Control unit 22 may further include an audio controller for playing sound files, such as voice activation commands, at one or more speaker 34.

Water purifier 210 in the illustrated embodiment also includes a user interface 220. Control unit 212 of water purifier 210 in an embodiment includes a video controller, which may have its own processing and memory for interacting with primary control processing and memory of control unit 212. User interface 220 includes a video monitor 222, which may likewise operate with a touch screen overlay placed onto video monitor 222 for inputting commands into control unit 212. User interface 220 may also include one or more electromechanical input device, such as a membrane switch or other button. Control unit 212 may further include an audio controller for playing sound files, such as alarm or alert sounds, at one or more speaker 224 of water purifier 210.

Cycler 20 operates with a disposable set 40 as illustrated. Disposable set 40 in the illustrated embodiment includes a disposable pumping cassette 42, which may include a planar rigid plastic piece covered on one or both sides by a flexible membrane. The membrane pressed against housing 24 of cycler 20 forms a pumping and valving membrane. Disposable cassette 42 includes fluid pump chambers 44 that operate with the pneumatic pump chambers located at housing 24 of cycler 20 and fluid valve chambers 46 that operate with the pneumatic valve chambers located at housing 24 of cycler 20.

In the illustrated embodiment, disposable set 40 includes a patient line 50 that extends from a patient line port of cassette 42 and terminates at a patient line connector 52. Patient line connector 52 connects to a patient transfer set 54, which in turn connects to an indwelling catheter located in the peritoneal cavity of patient P. Disposable set 40 includes a drain line 56 that extends from a drain line port of cassette 42 and terminates at a drain line connector 58. Drain line connector 58 connects to a mating port of water purifier 210 in the illustrated embodiment.

Disposable set 40 in the illustrated embodiment includes a heater/mixing line 60 that extends from a heater/mixing line port of cassette 42 and terminates at a heater/mixing bag 62 discussed in more detail below. Disposable set 40 includes an upstream water line segment 64a that extends to a first connector 66a of a water accumulator 66. A downstream water line segment 64b extends from a second connector 66b of water accumulator 66 to cassette 42. In the illustrated embodiment, upstream water line segment 64a begins at a water line connector 68 connected to water purifier 210 and is located upstream from water accumulator 66.

Water purifier 210 outputs water and possibly water suitable for peritoneal dialysis ("WFPD"). To ensure WFPD, however, a sterilizing grade filter 70a is placed upstream from a downstream sterilizing grade filter 70b, respectively. Filters 70a and 70b may be placed in water line segment 64a upstream of water accumulator 66. Sterilizing grade filters 70a and 70b may be pass-through filters that do not have a reject line. Pore sizes for the hydrophilic membranes of filters 70a and 70b may, for example, be less than a micron, such as 0.1 or 0.2 micron. Suitable sterilizing grade filters 70a and 70b may be provided by the assignee of the present disclosure. In an embodiment, only one of upstream or downstream sterilizing grade filter 70a and 70b is needed to produce WFPD, nevertheless, two sterilizing grade filters 70a and 70b are provided in the illustrated embodiment for redundancy in case one fails.

FIG. 1 further illustrates that a first concentrate container 84a holds a first, e.g., glucose, concentrate, which is pumped from container 84a through a container line 86 to a first to disposable pumping cassette 42. A second concentrate container 84b holds a second, e.g., buffer, concentrate, which is pumped from container 84b through a container line 88 to disposable cassette 42.

In an embodiment, to begin treatment, patient P loads cassette 42 into cycler 20 and in a random or designated order (i) places heater/mixing bag 62 onto cycler 20, (ii) connects upstream water line segment 64a to water purifier 210, (iii) connects drain line 56 to a drain connector of water purifier 210, (iv) connects first concentrate container 84a to disposable cassette 42, and (v) connects second concentrate container 84b to cassette 42. At this point, patient connector 52 is still capped. Once fresh dialysis fluid is prepared and verified, patient line 50 is primed with fresh dialysis fluid, after which patient P may connect patient line connector 52 to transfer set 54 for treatment. Each of the above steps may be illustrated graphically at video monitor 32 and/or be provided via voice guidance from speakers 34.

Control unit 22 may be programmed to cause cycler 20 to perform one or more mixing action to help mix dialysis fluid properly and homogeneously for treatment. For example, any of fluid pump chambers 44 may be caused to withdraw into the pump chambers some amount of mixed fluid (e.g., made from one or both first and second concentrates 84a, 84b and WFPD) from heater/mixing bag 62 and send such mixture back to heater/mixing bag 62 and repeat this procedure multiple times (described herein as a mixing sequence or "waffling"). In particular, to perform a mixing sequence, control unit 22 in an embodiment causes cycler 20 to close all fluid valve chambers 46 at cassette 42 except for the fluid valve chamber 46 to heater/mixing line 60 and heater/mixing bag 62. Fluid pump chambers 44 are stroked sequentially and repeatedly (i) pulling a possibly unmixed fluid combination of WFPD and concentrates from heater/mixing bag 62 into the pump chambers, followed by (ii) pushing the mixed WFPD and concentrates from the pump chambers back to heater/mixing bag 62 and (iii) repeating (i) and (ii) at least one time. Control unit 22 may be programmed to stroke fluid pump chambers 44 together so that they both pull and push at the same time, or alternatingly so that one pump chamber 44 pulls from heater/mixing bag 62, while the other pump chamber 44 pushes to heater/mixing bag 62, creating turbulence in heater/mixing line 60.

Due to the construction of heater/mixing container or bag 62, cassette 42 and heater/mixing line 60, the WFPD from accumulator 66 and concentrates from first and second concentrate containers 84a and 84b are already at least partially mixed before entering the container or bag. Even if cassette 42 is not provided, the WFPD and at least one concentrate will therefore mix partially in heater/mixing line 60 prior to reaching the container or bag.

FIG. 1 further illustrates that cycler 20 rests on a leveling tray 100 of the present disclosure. As illustrated in detail below, leveling tray 100 enables housing 24 of cycler 20 to be leveled and for the heater/mixing pan 36 of the housing to be set at a desired angle, so that heater/mixing bag 62 resting on the heater/mixing pan 36 is likewise set at the desired angle. FIG. 1 also illustrates that leveling tray 100 provides hooks or hooking mechanisms upon which bags or containers, such as water accumulator 66 and concentrate containers 84a and 84b, may be hung for convenience and to extend vertically, which is desirable from an air collection standpoint. The hanging of bags or containers 66, 84a and 84b also allows the associated tubing 64a, 64b, 86 and 88 to extend in an organized manner.

Leveling Apparatus and Methodology

Figure 2:
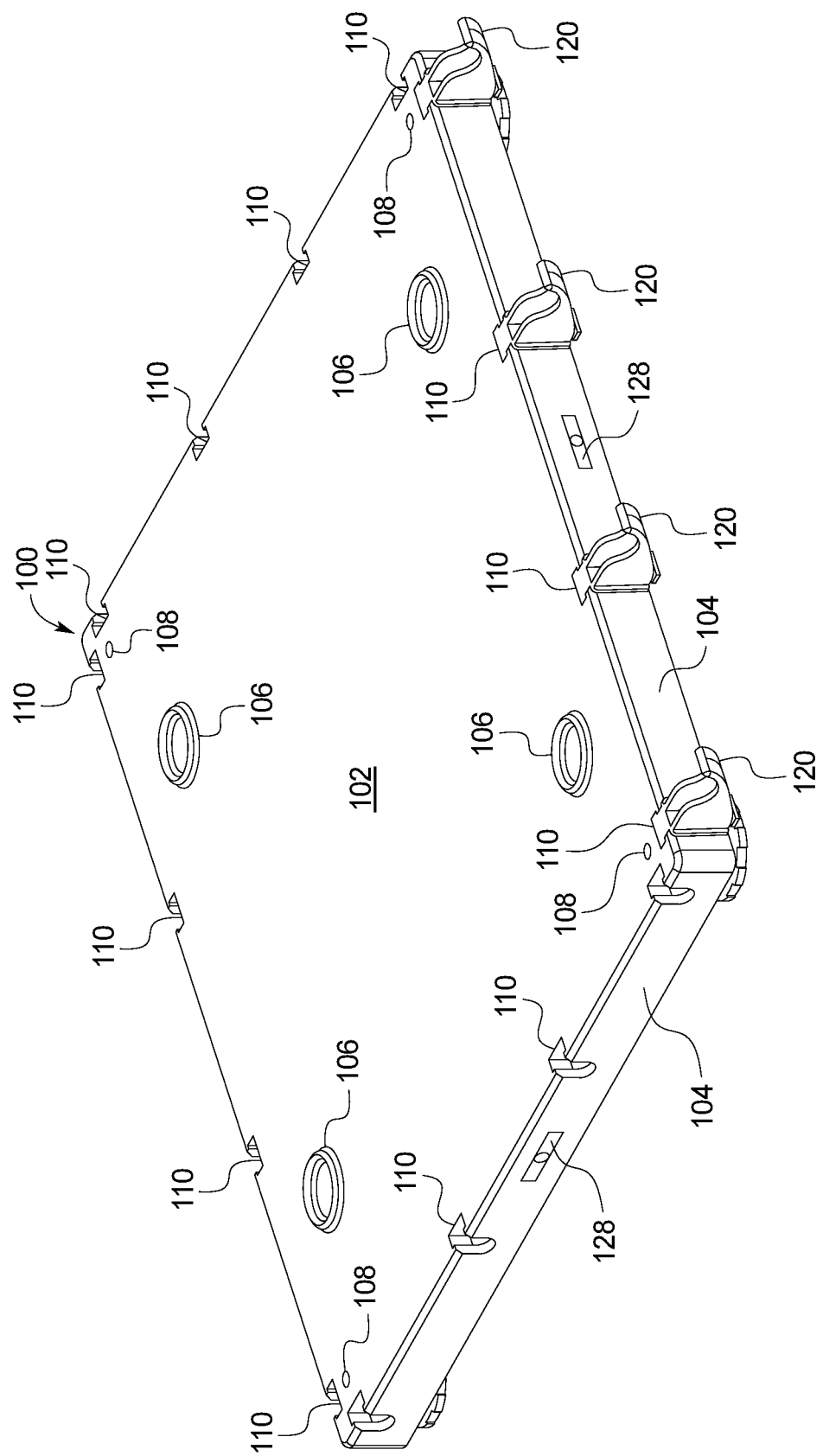
FIG. 2 is a top-front perspective view of one embodiment of a leveling tray illustrated in connection with the system of FIG. 1.

Referring now to FIG. 2, leveling tray 100 is illustrated in more detail. Leveling tray may be made of metal or plastic. If metal, leveling tray 100 may be aluminum, steel or stainless steel. If plastic, leveling tray 100 may be any moldable or 3D printable plastic, such as, acrylonitrile butadiene styrene ("ABS"), polypropylene ("PP"), polyethylene ("PE"), polyvinyl chloride ("PVC") or polyurethane ("PU"). Certain views below show surface 102 of leveling tray 100 as a thickened block of material having sides 104 and forming female threads to receiving leveling feet. In alternative embodiments, surface 102 of leveling tray 100 may be a molded or printed (plastic) or formed (metal), thinner walled structure having a top and sides 104 formed for rigidity and having threaded bosses (molded, printed or formed) or straight walled bosses press-fitted with metal (e.g., steel or stainless steel threaded inserts).

FIG. 2 illustrates that surface 102 of leveling tray 100 in one embodiment is formed or provided with indents 106, e.g., circular indents, for receiving at least a portion of an object, e.g., machine or cycler 20, placed onto surface 102 to hold the object in place and to tend to prevent sliding. In an embodiment, machine or cycler 20 is provided with mounting feet that may be circular or have another desired foot shape. Indents 106 are sized and shaped accordingly to accept the mounting feet and are spaced apart in the same footprint as the mounting feet.

FIG. 2 also illustrates that surface 102 of leveling tray 100 in one embodiment is formed or provided with apertures 108, e.g., circular apertures, for accessing a tightening member of a leveling foot described in more detail below. The user may use a tool, such as a screw driver, hex driver or Allen wrench, to tighten or loosen the tightening member and do so from the top of surface 102. It should be appreciated that surface 102 is larger than the corresponding length and depth dimensions of machine or cycler 20, such that a border is formed at least partially around the length and depth dimensions to form apertures 108 as illustrated in FIG. 1. In an alternative embodiment in which the leveling feet are attached instead directly to machine or cycler 20, and leveling tray 100 is not provided, apertures 108 may instead be provided in lower ledges provided on the walls of housing 24 of medical device or cycler 20.

FIG. 2 further illustrates that surface 102 and sides 104 of leveling tray 100 include or define mounting cavities 110 for accepting removable hooks 120. In the illustrated embodiment, four mounting cavities 110 per side 104 are provided, while only four hooks 120 are provided. As illustrated in FIG. 1, two concentrate bags 84a and 84b and a water accumulator 66 may be used. A last bag of solution may also be used. Four hooks 120 should therefore be sufficient, although tray 100 may hold up to sixteen hooks 120. Providing extra mounting cavities 110 enables the user or patient to space the bags apart and place them in convenient locations about surface 102. Hooks 120 may alternatively be formed integrally with surface 102 of tray 100, or mounting cavities 110 may alternatively be mounting projections that accept like-fitting cavities formed in hooks 120.

FIG. 1 illustrates that machine or cycler 20 may include an onboard electrically outputting level detector 28. FIG. 2 illustrates that leveling tray 100 or machine 20 may alternatively or additionally include one or more manually observed level detector or level 128, such as a bubble type level 128. In the illustrated embodiment, manually observed levels 128 are placed in the middle of (i) front side 104 of surface 102 for length dimension (left to right) leveling and (ii) right side 104 of surface for depth dimension (front to back) leveling. If leveling tray 100 is not used and the leveling feet discussed below are provided instead with machine or cycler 20, then one or more manually observed level 128 may be placed in like locations along housing 24.

The patient or caregiver uses manually observed levels 128 with the leveling feet in the known manner. Electrically outputting level detector 28 may operate with control unit 22, which in turn operates with user interface 30, which may provide an audio, visual or audiovisual message guiding the user as to which leveling foot to adjust and in which direction. When electrically outputting level detector 28 senses that cycler or machine 20 is in a desired leveling position, or within a specified percentage of same, user interface 30 so notifies the patient or caregiver in one embodiment.

Figure 3:
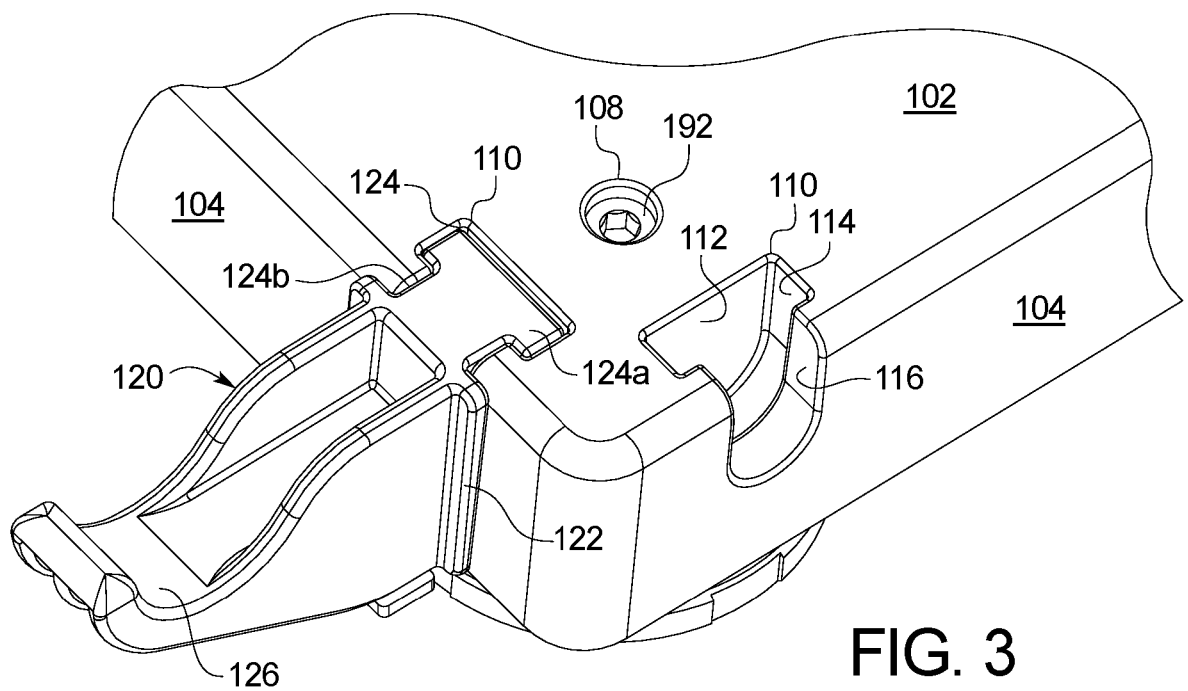
FIG. 3 is a top-front perspective cutaway view of a corner of the leveling tray illustrated in FIG. 2 showing various embodiments of a removable hook and a mounting cavity for accepting the hook.
Figure 4:
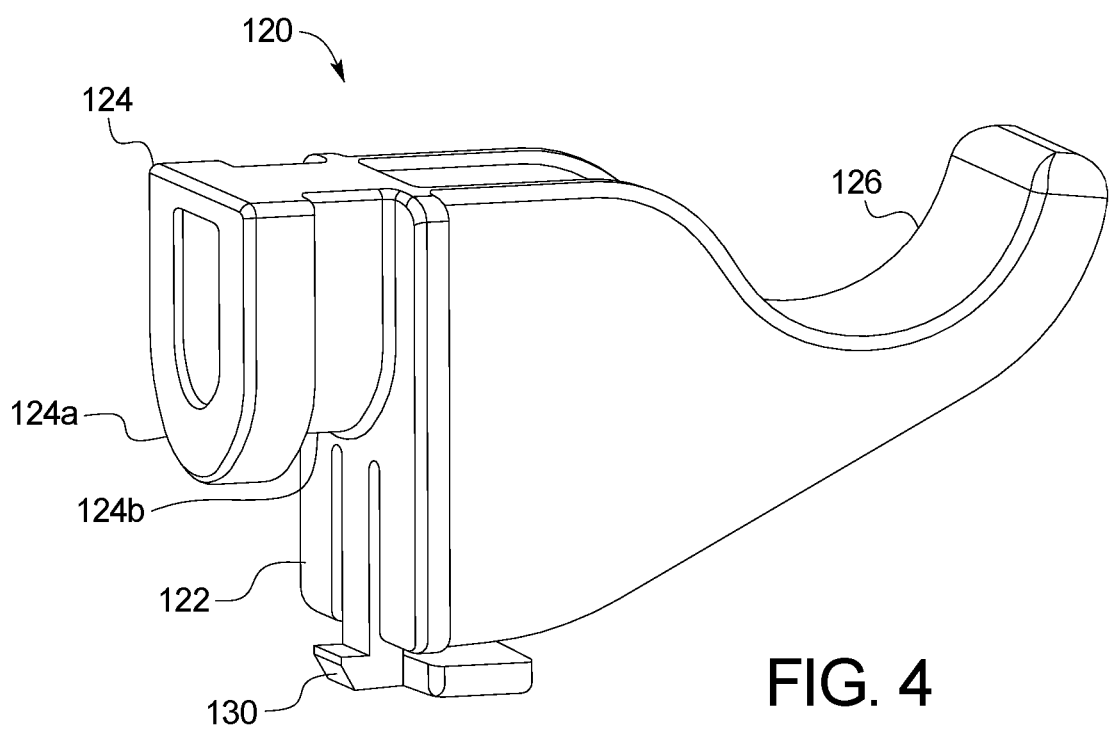
FIG. 4 is a top-side perspective view of one embodiment of the hook illustrated in illustrated in FIG. 3.

FIGS. 3 and 4 illustrate mounting cavities 110 and removable hooks 120 in more detail. Removable hooks 120 may be made of any one or more material listed above and may be molded or 3D printed (plastic) or machined or cast (metal). FIG. 3 also illustrates an embodiment for the placement of apertures 108, which is also the location of leveling feet as shown below. The hex head 192 of the tightening member of the associated leveling foot may is seen beneath aperture 108 in FIG. 3. In the illustrated embodiment, the patient or user accordingly uses a hex driver or Allen wrench to tighten or loosen the leveling foot.

FIG. 3 illustrates an empty mounting cavity 110 on the right and a mounting cavity 110 on the left that currently holds or is engaged with a removable hook 120. The mounting cavities in the illustrated embodiment include an inner wall 112, a larger radius slot 114 extending from inner wall 112, and a smaller radius slot 116 extending from larger radius slot 114.

FIGS. 3 and 4 illustrate that removable hooks 120 in one embodiment include an abutment wall 122 that abuts a side 104 of surface 102 when mounted to leveling tray 100. A mounting tab 124 extends in a leveling tray mounting direction from abutment wall 122. Mounting tab 124 includes a larger radius tab portion 124a and smaller radius tab portion 124b. Larger radius tab portion 124a fits into larger radius slot 114 of empty mounting cavity 110, while smaller radius tab portion 124b fits into smaller radius slot 116 of empty mounting cavity 110 when removable hook 120 is inserted into the empty mounting cavity 110. Larger radius slot 114 and smaller radius slot 116 of empty mounting cavity 110 bear the brunt of the weight of the container or bag hanging from hook 120.

A hanging member 126 extends in a bag or container hanging direction from abutment wall 122. Hanging member 126 as illustrated may be formed with a curved or "J" shape to help prevent the bag or container from slipping off of hanging member 126 inadvertently. Hanging member 126 extends far enough outwardly that the bag or container hanging from member 126 hangs down without interruption from a side of the structure upon which leveling tray 100 and machine 20 are supported.

A locking hook 130 is located below abutment wall 122 and extends in the leveling tray mounting direction (same as mounting tab 124) from the abutment wall. As illustrated perhaps best in FIGS. 5 and 6, locking hook 130 extends beneath the respective side 104 of surface 102 and locks removable hook 120 into place from the standpoint that the hook may not be removed vertically from mounting cavity 110 without first rotating locking hook 130 out from underneath side 104 of surface 102. To remove hook 120 from leveling tray 100, the user rotates locking hook 130 out from underneath side 104 of surface 102 and then lifts mounting tab 124 from mounting cavity 110. Hook 120 is accordingly easily inserted into and removed from mounting cavity 110 of leveling tray 100.

Figure 5:
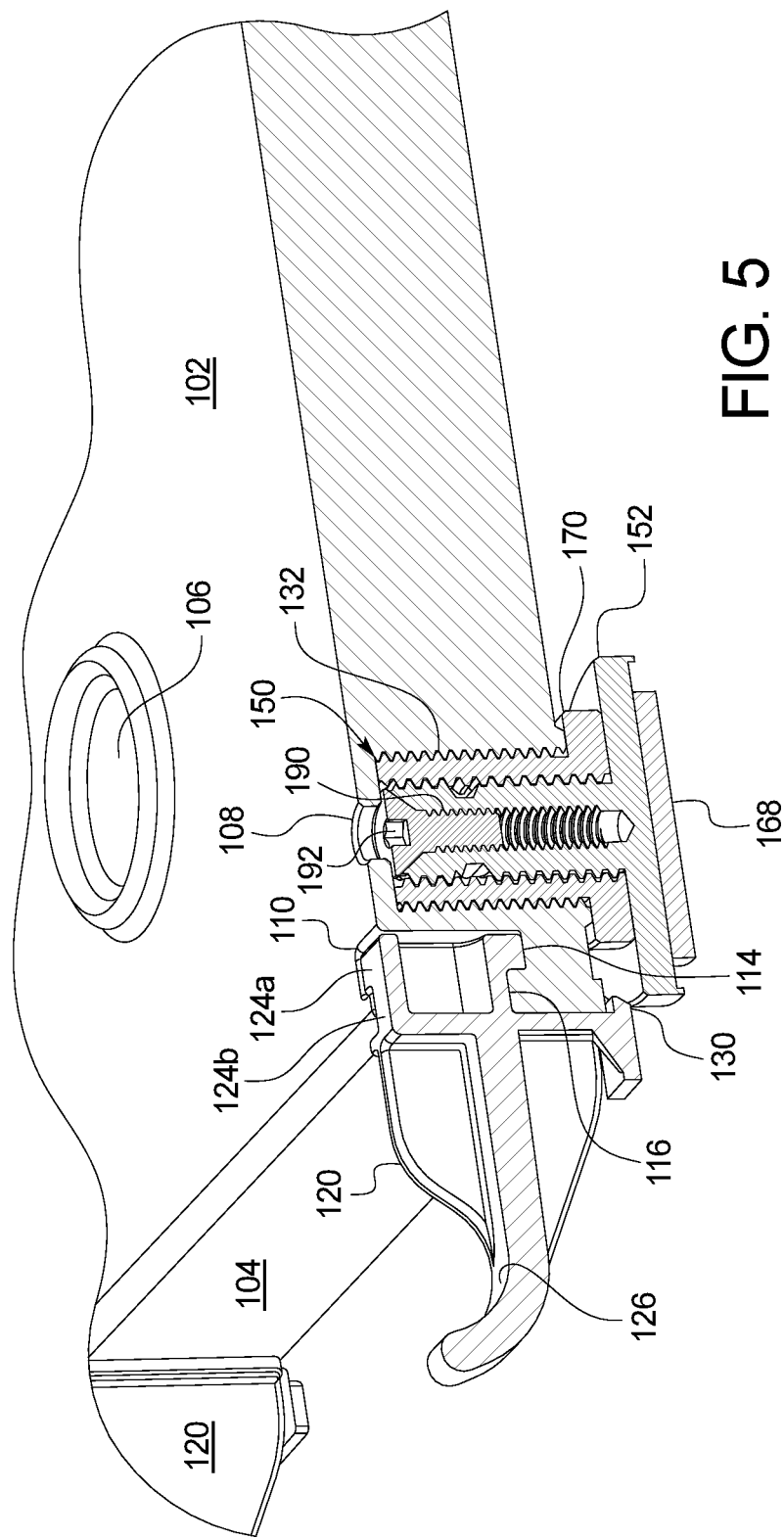
FIG. 5 is a top-front perspective cutaway and sectioned view of a corner of the leveling tray illustrated in FIG. 2 showing various embodiments of the removable hook and a telescoping leveling foot of the present disclosure in a retracted state.
Figure 6:
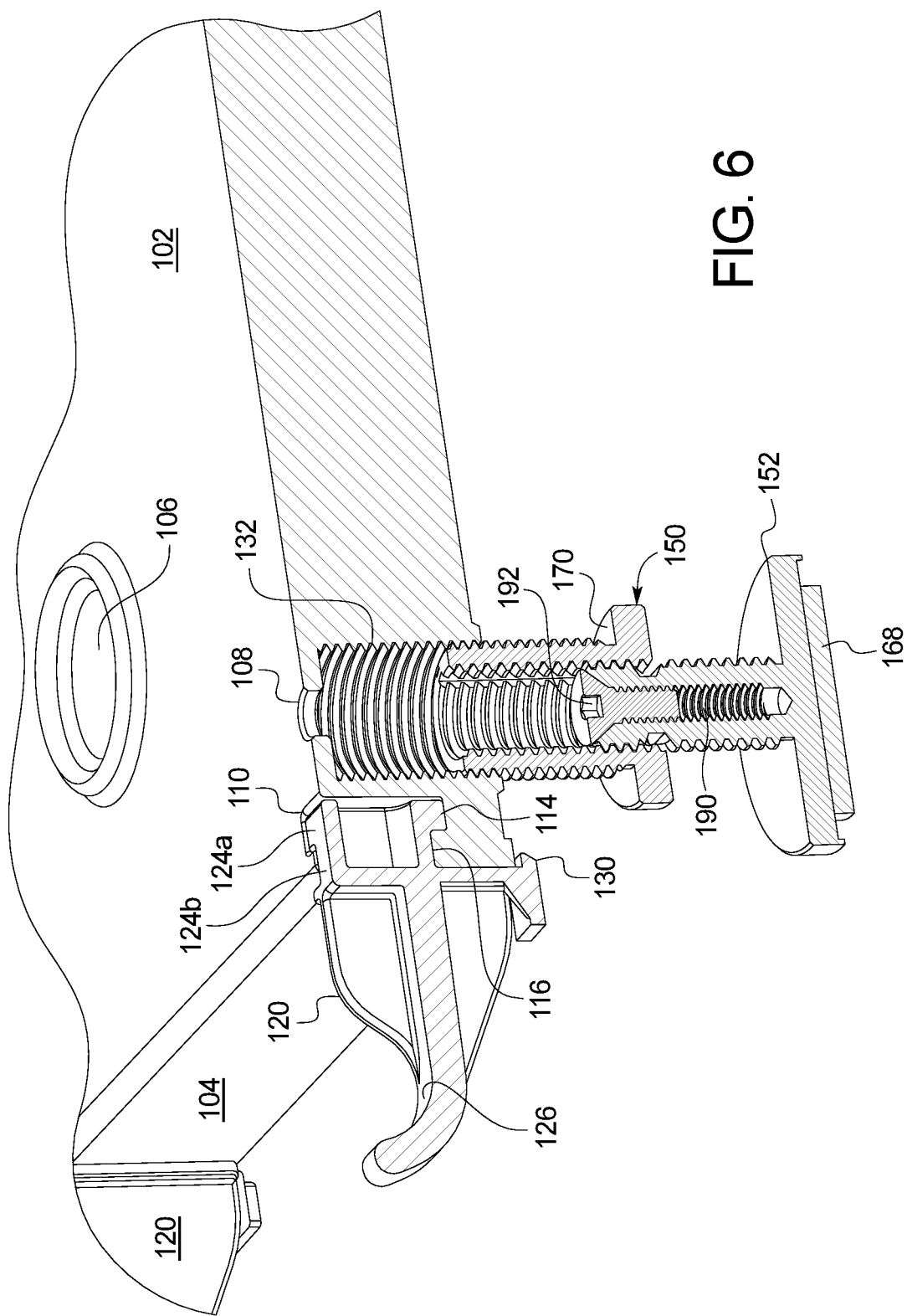
FIG. 6 is a top-front perspective cutaway and sectioned view of a corner of the leveling tray illustrated in FIG. 2 showing various embodiments of the removable hook and a telescoping leveling foot of the present disclosure in an extended state.

FIGS. 5 and 6 also illustrate an embodiment of leveling foot 150. As illustrated, the central axis of leveling foot 150 is in one embodiment aligned with the center of aperture 108. FIG. 2 shows leveling tray 100 having four apertures 108. Leveling tray 100 may therefore have up to four leveling feet 150, which are each threaded into female threads 132 formed in surface 102 of leveling tray 100 via any of the embodiments described above. In an embodiment, female threads 132 are 3/4-16. Leveling feet including three primary components including an inner cylindrical member 152, an outer cylindrical member 170 and a tightening member 190. In FIG. 5, leveling foot 150 is in a fully retracted position in which outer cylindrical member 170 is threaded fully downwardly onto inner cylindrical member 152 and leveling tray 100 is threaded fully downwardly onto outer cylindrical member 170. As is illustrated in FIG. 5, leveling foot 150 maintains a low profile relative to the amount of height adjustment that it provides.

FIG. 6 illustrates both of the first and second height adjustments of leveling foot 150. Here, outer cylindrical member 170 is threaded up along inner cylindrical member 152 (first height adjustment), while leveling tray 100 is threaded up along outer cylindrical member 170 (second height adjustment). The user turns outer cylindrical member 170 counterclockwise to thread member 170 up along inner cylindrical member 152 and clockwise to thread member 170 down along inner cylindrical member 152. Conversely, user turns inner cylindrical member 152 clockwise to thread leveling tray 100 up along outer cylindrical member 170 and counterclockwise to thread leveling tray 100 down along outer cylindrical member 170. In essence, the user backs leveling foot 150 out of leveling tray 100 by turning inner cylindrical member 152 clockwise to raise leveling tray 100 relative to leveling foot 150.

FIGS. 5 and 6 both illustrate tightening member 190, which includes third male threads sized to be threaded into the female threads provided by the inner cylindrical member 152. In an embodiment, the male threads of tightening member 190 are 10-24. In the illustrated embodiment, tightening member 190 is a flathead screw having a hexagonal screw head 192. Tightening member 190 may alternatively be a different type of screw and have a different type of screw head, e.g., flathead or Philips head. Inner cylindrical member 152, outer cylindrical member 170 and tightening member 190 may each be made of any one or more material listed above and may be molded or 3D printed (plastic) or machined or cast (metal).

In FIG. 5, tightening member 190 may be turned counterclockwise to loosen the member to allow adjustment of leveling foot 150. In FIG. 6, after leveling foot 150 has been adjusted, tightening member 190 may be turned clockwise to tighten the member to hold or loosely lock leveling foot 150 in the desired, adjusted position. The effect of turning tightening member 190 is discussed in more detail below.

Figure 7:
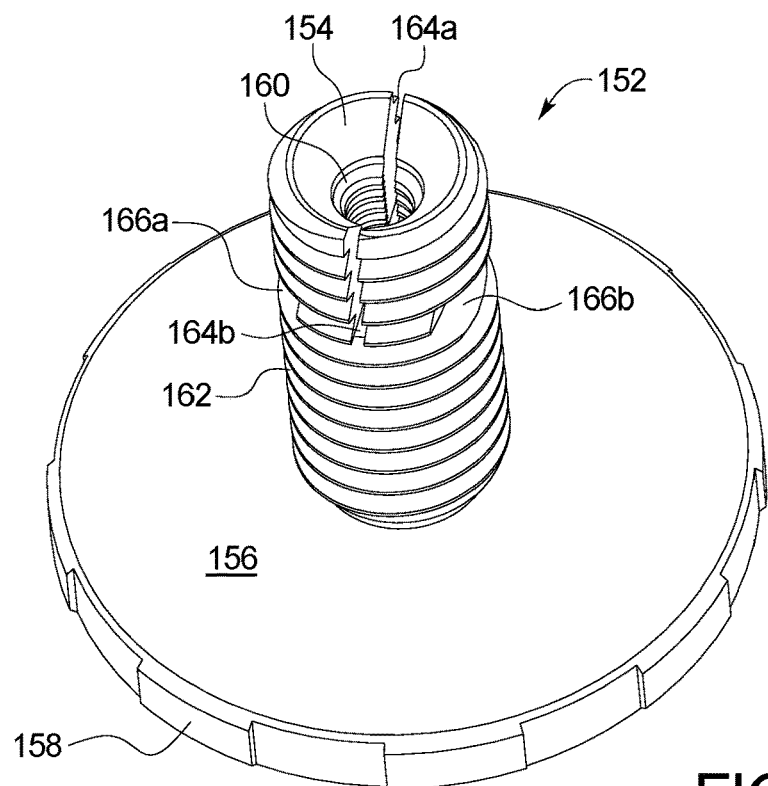
FIG. 7 is a top-front perspective view of one embodiment for an inner cylindrical member of the telescoping leveling foot of the present disclosure.
Figure 8:
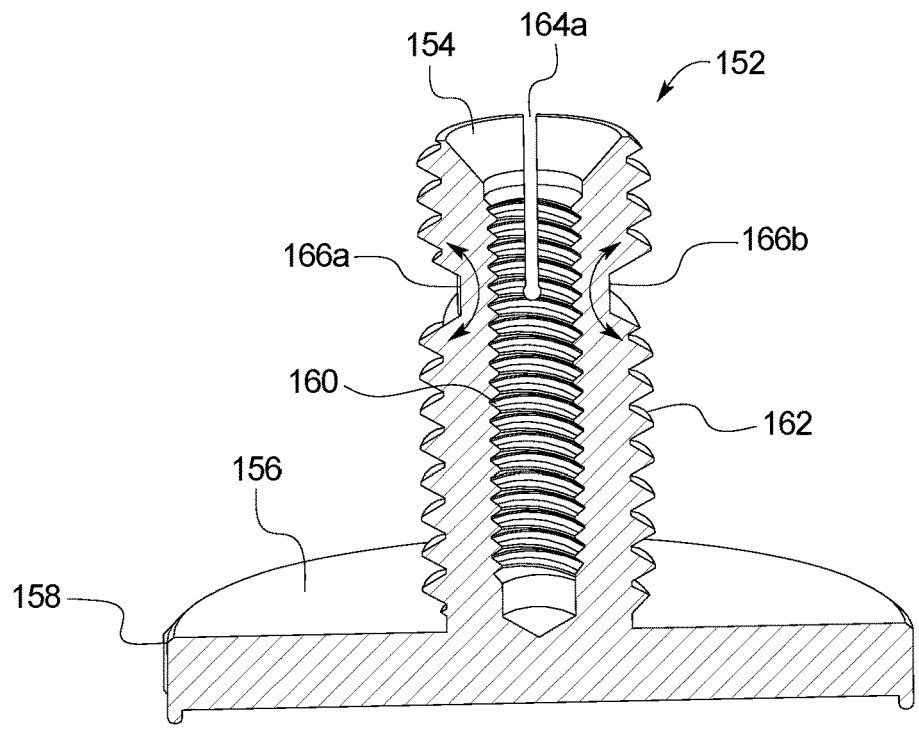
FIG. 8 is a side elevation sectioned view of the inner cylindrical member of FIG. 7.

FIGS. 7 and 8 illustrate inner cylindrical member 152 in more detail. Inner cylindrical member 152 in the illustrated embodiment includes a cylindrical body 154 and a circular flange 156 extending from a base of the cylindrical body. The outer edge of circular flange 156 may include knurls or other features 158 to aid a user in turning inner cylindrical member 152 via circular flange 156. The inner surface of cylindrical body 154 includes or defines female threads 160, which in an embodiment are 10-24. The outer surface of cylindrical body 154 includes or defines male threads 162, which in an embodiment are ½-13. FIGS. 5 and 6 also illustrate that the bottom of inner cylindrical member 152 may be fitted with a rubber or otherwise high coefficient of friction material pad 168.

Cylindrical body 154 also includes or defines plural partial slits 164a and 164b forming plural cylindrical sections that hinge outwardly when tightening member 190 is threaded into female threads 160. FIG. 7 and in particular FIG. 8 illustrate that weakening indents 166a and 166b are provided longitudinally at the beginnings of slits 164a and 164b, and which are rotated 90° from slits 164a and 164b. Weakening indents 166a and 166b aid the outward hinging action of the plural cylindrical sections as indicated by the arrows in FIG. 8.

Figure 9:
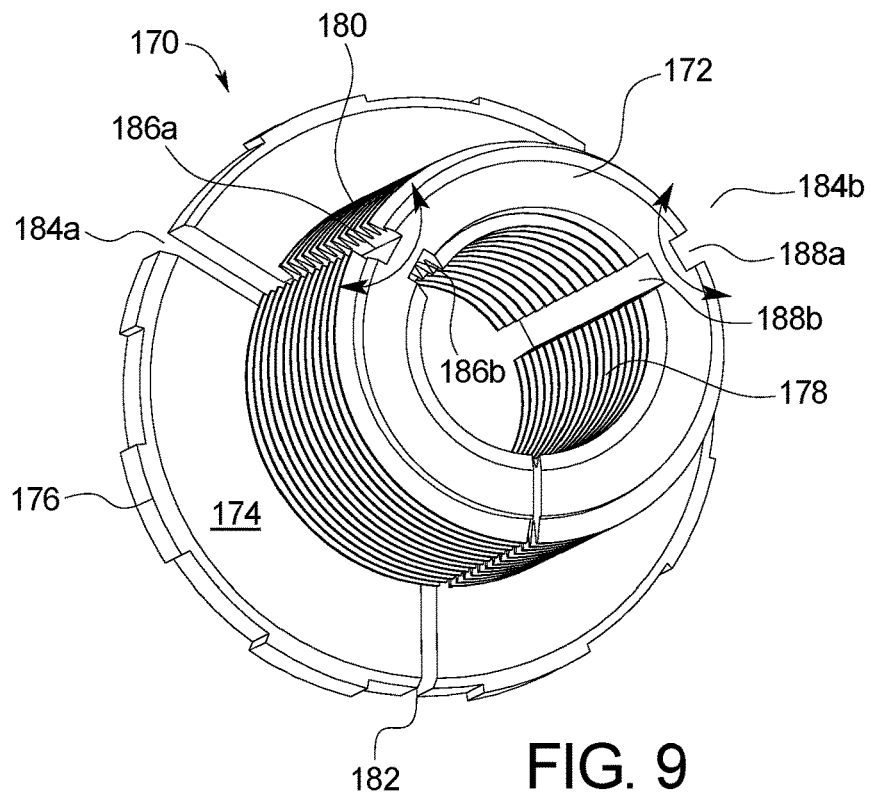
FIG. 9 is a top-front perspective view of one embodiment for an outer cylindrical member of the telescoping leveling foot of the present disclosure.
Figure 10:
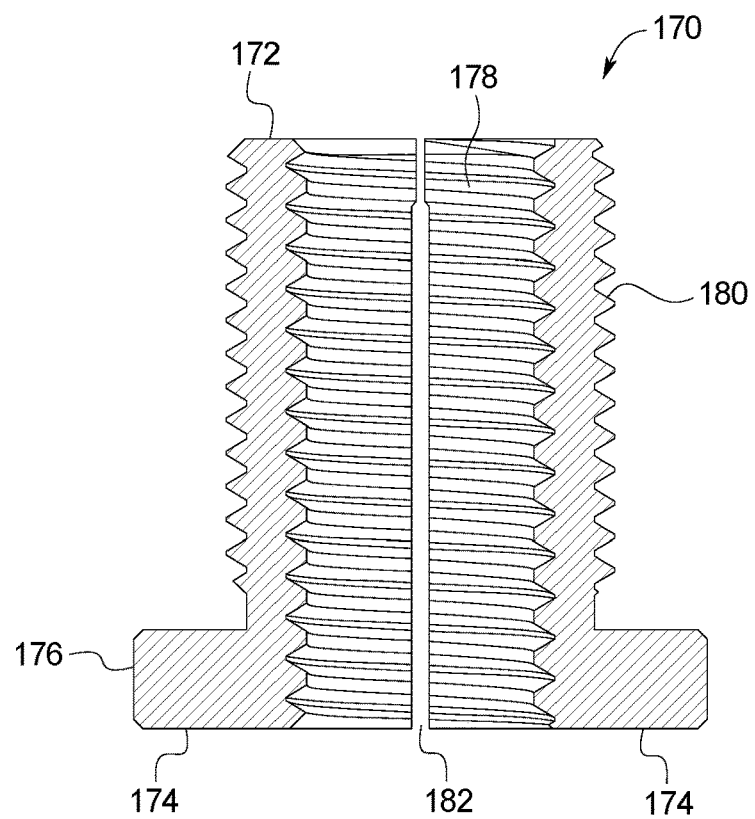
FIG. 10 is a side elevation sectioned view of the outer cylindrical member of FIG. 9.

FIGS. 9 and 10 illustrate outer cylindrical member 170 in more detail. Outer cylindrical member 170 in the illustrated embodiment includes a cylindrical body 172 and a circular flange 174 extending from a base of the cylindrical body. The outer edge of circular flange 174 may also include knurls or other features 176 to aid a user in turning outer cylindrical member 170 via circular flange 174. The inner surface of cylindrical body 172 includes or defines female threads 178, which in an embodiment are ½-13. The outer surface of cylindrical body 172 includes or defines male threads 180, which in an embodiment are ¾-16.

Cylindrical body 172 also includes or defines a full slit 182 that enables outer cylindrical member 170 to spread open when the plural cylindrical sections of the inner cylindrical member 152 hinge outwardly. FIG. 9 illustrates that outer cylindrical member 170 further includes (i) slits 184a and 184b extending radially through circular flange 174. Slits 182, 184a and 184b may be spaced apart radially equally at 120° from each other. Slit 184a extends to a weakening groove 186a formed along the outer surface of cylindrical body 172. A like weakening groove 186b is formed opposite weakening groove 186a on the inner surface of cylindrical body 172. Likewise, slit 184b extends to a weakening groove 188a formed along the outer surface of cylindrical body 172. A like weakening groove 188b is formed opposite weakening groove 188a on the inner surface of cylindrical body 172.

Weakening grooves 186a, 186b, 188a and 188b and full slit 182 enable outer cylindrical body 172 to expand and retract about the thin stretches of material existing between (i) weakening grooves 186a and 186b and (ii) weakening grooves 188a and 188b as indicated by the arrows in FIG. 9. When outer cylindrical body 172 expands about the thin stretches of material, slits 184a and 184b enable the bordering sections of the slits to come together, while the bordering sections of circular flange 174 at full slit 182 spread apart.

As illustrated perhaps best in FIG. 8, the top of cylindrical body 154 of inner cylindrical member 152 may include a female flathead shape similar to or the same as the flathead shape of screw head 192 of tightening member 190. When tightening member 190 is tightened or threaded into female threads 160 of inner cylindrical member 152, screw head 192 presses down into the female threads 160, causing the slit sections of cylindrical body 154 to spread open, which in turn cause the slit sections of cylindrical body 172 of outer cylindrical member 170 to spread open. The above motions bind the adjoining threads, making further turning of the mating threads difficult, thereby loosely locking leveling foot 150 in place. Male threads 162 bind against female threads 178, while male threads 180 bind against female threads 132 formed in surface 102 of leveling tray 100. Turning tightening member 190 in the loosening direction undoes the above-described thread binding, so that leveling foot 150 may be readjusted.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims. For example, the leveling feet of the present disclosure are not limited to medical fluid delivery applications. The leveling feet may be used instead in any commercial, industrial or home application requiring a level surface or a desired pitch for the structure being supported. In an alternative embodiment, a tapered pipe thread and plug may be used in place of tapped and countersunk hole for inner cylindrical member 152. Provisions may be made in each foot 150, so that they may not come completely unscrewed and disengaged, such as (i) providing fingers that expand into a counterbore in the female thread, which allow assembly but not unscrewing at an extreme of travel or (ii)

providing an external retaining ring at the beginning of the thread that stops on a counterbore in the mating female thread at the extreme of travel.

The invention is claimed as follows:

1. A medical fluid delivery system comprising:
a source of purified water;
a source of concentrate for mixing with water from the source of purified water;
a disposable set including
a pumping portion,
a water line in fluid communication with the source of purified water and the pumping portion,
a concentrate line in fluid communication with the source of concentrate and the pumping portion, and
a mixing container in fluid communication with the pumping portion;
a medical fluid delivery machine including,
a pump actuator operable with the pumping portion of the disposable set, and
a mixing pan configured to support the mixing container;
a leveling tray upon which the medical fluid delivery machine is set for treatment, the leveling tray including at least one aperture including female threads; and
at least one leveling foot connected respectively to the at least one aperture of the leveling tray and positioned and arranged such that the mixing pan is oriented at a desired pitch or level for mixing the concentrate and the purified water, wherein the at least one leveling foot includes:
an outer cylindrical member including (i) male threads on an exterior surface for engaging the female threads of the respective aperture to enable the outer cylindrical member to telescope with respect to the leveling tray, (ii) female threads on an interior surface, and (iii) a circular flange extending from a base of the outer cylindrical member,
an inner cylindrical member including (i) male threads on an exterior surface for engaging the female threads of the respective outer cylindrical member to enable the inner cylindrical member to telescope with respect to the outer cylindrical member, (ii) female threads on an interior surface, and (iii) a circular flange extending from a base of the inner cylindrical member, and
a tightening member including male threads on an exterior surface for engaging the female threads of the respective inner cylindrical member to enable locking of a telescoping position of the inner cylindrical member and the outer cylindrical member.

2. The medical fluid delivery system of claim 1, wherein the at least one leveling foot is connected to a housing of the medical fluid delivery machine.

3. The medical fluid delivery system of claim 1, wherein the leveling tray is provided with at least one hook for supporting at least one fluid container, including a container for the source of concentrate.

4. The medical fluid delivery system of claim 3, wherein the source of purified water includes a water purifier or a container for the purified water, and wherein when the source of purified water includes the container for the purified water, the at least one hook is configured to support the container for the purified water.

5. The medical fluid delivery system of claim 3, wherein the leveling tray includes at least one hook receiving location positioned and arranged to removeably receive the at least one hook.

6. The medical fluid delivery system of claim 1, wherein the leveling tray includes a border extending from the medical fluid delivery machine, the border forming the at least one aperture allowing access to adjust the at least one leveling foot.

7. The medical fluid delivery system of claim 1, wherein the medical fluid delivery machine or the leveling tray includes a level detector.

8. The medical fluid delivery system of claim 1, wherein the medical fluid delivery machine includes a control unit and a level detector in operable communication with the control unit.

9. The medical fluid delivery system of claim 8, wherein the medical fluid delivery machine includes a user interface in operable communication with the control unit, the control unit configured to generate at least one audio, visual or audiovisual message via the user interface based upon communication with the level detector.

10. The medical fluid delivery system of claim 1, wherein the tightening member includes a head configured to be grasped and turned by a user to tighten or loosen at least one of (i) the inner cylindrical member relative to the outer cylindrical member, or (ii) the outer cylindrical member relative to the leveling tray.

11. The medical fluid delivery system of claim 1, wherein the inner cylindrical member includes slits forming cylindrical sections that hinge outwardly when the tightening member is threaded into the female threads of the inner cylindrical member.

12. The medical fluid delivery system of claim 11, wherein the outer cylindrical member includes a slit enabling the outer cylindrical member to spread open when the cylindrical sections of the inner cylindrical member hinge outwardly.

13. The medical fluid delivery system of claim 12, wherein the outer cylindrical member further includes at least one weakening groove enabling the outer cylindrical member to spread open about the at least one weakening groove.

* * * * *